United States Patent
Sekino et al.

(10) Patent No.: US 11,051,764 B2
(45) Date of Patent: Jul. 6, 2021

(54) DEVICE FOR DETECTING BLOOD FLOW DISTURBANCE

(71) Applicants: Masaki Sekino, Tokyo (JP); Yoko Tomioka, Tokyo (JP); Takao Someya, Tokyo (JP); PARAMOUNT BED CO., LTD., Tokyo (JP); KANEKA CORPORATION, Osaka (JP)

(72) Inventors: Masaki Sekino, Tokyo (JP); Yoko Tomioka, Tokyo (JP); Yusuke Inoue, Tokyo (JP); Takao Someya, Tokyo (JP); Shinri Sakai, Tokyo (JP); Shintaro Enomoto, Tokyo (JP)

(73) Assignees: PARAMOUNT BED CO., LTD., Tokyo (JP); KANEKA CORPORATION, Osaka (JP)

(*) Notice: Subject to any disclaimer, the term of this patent is extended or adjusted under 35 U.S.C. 154(b) by 589 days.

(21) Appl. No.: 15/889,457

(22) Filed: Feb. 6, 2018

(65) Prior Publication Data
US 2018/0160987 A1 Jun. 14, 2018

Related U.S. Application Data

(63) Continuation of application No. PCT/JP2016/073099, filed on Aug. 5, 2016.

(30) Foreign Application Priority Data

Aug. 7, 2015 (JP) .............................. JP2015-157488

(51) Int. Cl.
*A61B 5/00* (2006.01)
*A61B 5/026* (2006.01)
(Continued)

(52) U.S. Cl.
CPC .......... *A61B 5/7278* (2013.01); *A61B 5/0261* (2013.01); *A61B 5/1032* (2013.01);
(Continued)

(58) Field of Classification Search
CPC ... A61B 5/7278; A61B 5/0261; A61B 5/1032; A61B 5/7282; A61B 5/413;
(Continued)

(56) References Cited

U.S. PATENT DOCUMENTS

| 4,524,778 A | * | 6/1985 | Brown, Jr. | ............. A61B 5/015 374/E11.022 |
| 6,043,406 A | * | 3/2000 | Sessions | ............... A61F 13/023 602/41 |

(Continued)

FOREIGN PATENT DOCUMENTS

| CN | 100381095 C | 4/2008 |
| CN | 101232846 A | 7/2008 |

(Continued)

OTHER PUBLICATIONS

Weija et al. (In Vivo Reflectance of Blood and Tissue as a Function of Light Wavelength, IEEE Transactions on Biomedical Engineering. vol. 37. No. 6., pp. 632-639 (Year: 1990).*

(Continued)

*Primary Examiner* — Jacqueline Cheng
*Assistant Examiner* — Tho Q Tran
(74) *Attorney, Agent, or Firm* — Osha Bergman Watanabe & Burton LLP

(57) ABSTRACT

A blood flow disorder detection device includes: a sensor sheet including a flexible substrate and a plurality of sensors provided on the flexible substrate; and an analyzer that analyzes outputs of the plurality of sensors. The plurality of sensors measure different types of blood flow information of a living tissue, the blood flow information being obtained by (Continued)

attaching the sensor sheet to the living tissue. The analyzer detects a blood flow disorder in the living tissue by analyzing the different types of blood flow information from the plurality of sensors.

8 Claims, 11 Drawing Sheets

(51) Int. Cl.
| | |
|---|---|
| *A61B 5/01* | (2006.01) |
| *A61B 5/0205* | (2006.01) |
| *A61B 5/024* | (2006.01) |
| *G01J 3/50* | (2006.01) |
| *A61B 5/103* | (2006.01) |
| *G01F 9/00* | (2006.01) |

(52) U.S. Cl.
CPC ............ *A61B 5/7282* (2013.01); *G01F 9/001* (2013.01); *G01J 3/50* (2013.01); *A61B 5/01* (2013.01); *A61B 5/02055* (2013.01); *A61B 5/02416* (2013.01); *A61B 5/02438* (2013.01); *A61B 5/413* (2013.01); *A61B 5/6832* (2013.01); *A61B 2505/05* (2013.01); *A61B 2562/063* (2013.01); *A61B 2562/066* (2013.01); *A61B 2562/164* (2013.01)

(58) Field of Classification Search
CPC . A61B 2562/066; A61B 5/01; A61B 5/02055; A61B 5/02416; A61B 5/02438; A61B 5/6832; A61B 2505/05; A61B 2562/063; A61B 2562/164; G01F 9/001; G01J 3/50
USPC ........................................................ 600/504
See application file for complete search history.

(56) References Cited

U.S. PATENT DOCUMENTS

| | | | |
|---|---|---|---|
| 6,631,288 B1 | 10/2003 | Bain et al. | |
| 6,859,658 B1 | 2/2005 | Krug | |
| 7,113,817 B1 | 9/2006 | Winchester, Jr. et al. | |
| 9,931,078 B2* | 4/2018 | Gonopolskiy | A61B 5/6833 |
| 10,169,860 B2* | 1/2019 | Spahn | A61B 5/445 |
| 2002/0111545 A1 | 8/2002 | Lindberg et al. | |
| 2007/0123756 A1 | 5/2007 | Kitajima et al. | |
| 2008/0200786 A1 | 8/2008 | Berndsen | |
| 2009/0259139 A1* | 10/2009 | Stepien | A61B 5/015 |
| | | | 600/549 |
| 2009/0306487 A1* | 12/2009 | Crowe | A61B 5/14551 |
| | | | 600/322 |
| 2010/0016733 A1 | 1/2010 | Smith et al. | |
| 2010/0125214 A1 | 5/2010 | Brown et al. | |
| 2010/0136093 A1 | 6/2010 | Mondoulet et al. | |
| 2010/0260821 A1 | 10/2010 | Dupont et al. | |
| 2010/0278738 A1* | 11/2010 | Sitzman | A61K 49/0008 |
| | | | 424/9.1 |
| 2013/0245394 A1 | 9/2013 | Brown et al. | |
| 2014/0052006 A1* | 2/2014 | Lee | A61B 5/7278 |
| | | | 600/479 |
| 2015/0157220 A1 | 6/2015 | Fish et al. | |
| 2015/0160048 A1 | 6/2015 | Schuessler | |
| 2015/0164592 A1 | 6/2015 | Elhawary et al. | |
| 2017/0128566 A1 | 5/2017 | Dupont et al. | |
| 2018/0103873 A1* | 4/2018 | Jacquet-Lagreze | |
| | | | A61B 5/02007 |
| 2018/0318413 A1 | 11/2018 | Dupont et al. | |
| 2019/0216354 A1* | 7/2019 | Sternberger | A61B 5/316 |
| 2019/0314495 A1 | 10/2019 | Dupont et al. | |
| 2020/0353072 A1 | 11/2020 | Dupont et al. | |

FOREIGN PATENT DOCUMENTS

| | | |
|---|---|---|
| CN | 101404929 A | 4/2009 |
| CN | 101951952 A | 1/2011 |
| CN | 104427926 A | 3/2015 |
| JP | H10-295676 A | 11/1998 |
| JP | H11104113 A | 4/1999 |
| JP | 2002-540869 A | 12/2002 |
| JP | 2007-105316 A | 4/2007 |
| JP | 201192305 A | 5/2011 |
| JP | 2012-508631 A | 4/2012 |
| JP | 2013-94222 A | 5/2013 |
| JP | 2015-112488 A | 6/2015 |
| WO | WO2010055155 A2 * | 5/2010 |

OTHER PUBLICATIONS

Weija et al., In Vivo Reflectance of Blood and Tissue as a Function of Light Wavelength, IEEE Transactions on Biomedical Engineering. vol. 37. No. 6. (Year: 1990).*

Lin et al., Tissue Oximetry Monitoring in Microsurgical Breast Reconstruction Decreases Flap Loss and Improves Rate of Flap Salvage, Plastic and Reconstructive Surgery, pp. 1080-1085 (Year: 2011).*

Salgado et al., Flap Monitoring and Patient Management, Plastic and Reconstructive Surgery, p. 295e-302e (Year: 2009).*

Office Action issued in corresponding Japanese Application No. 2017-534410; dated Apr. 21, 2020 (5 pages).

Office Action issued in corresponding Chinese Application No. 201680045862.3; dated Jun. 18, 2020 (14 pages).

Office Action issued in corresponding Chinese Application No. 201680045862.3 dated Jan. 14, 2021 (18 pages).

International Search Report issued in application No. PCT/JP2016/073099; dated Nov. 8, 2016 (2 pages).

International Preliminary Report on Patentability issued in application No. PCT/JP2016/073099; dated Feb. 22, 2018 (7 pages).

* cited by examiner

FIG. 12
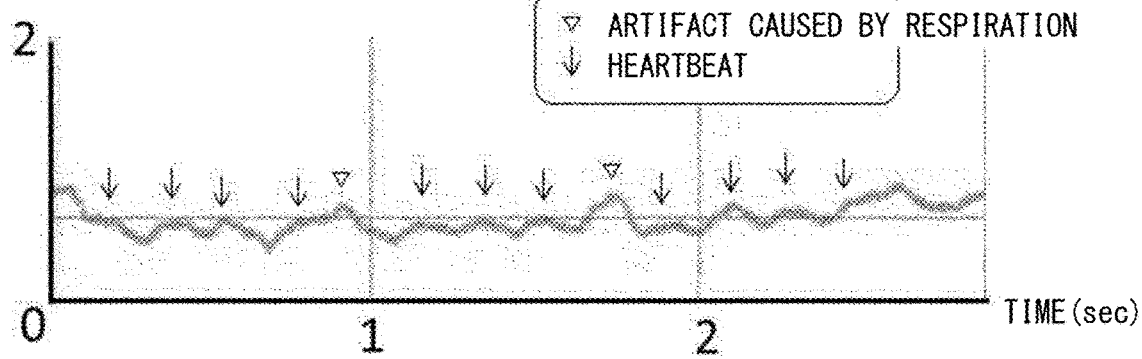
(a) BEFORE ISCHEMIA PULSES DETECTED
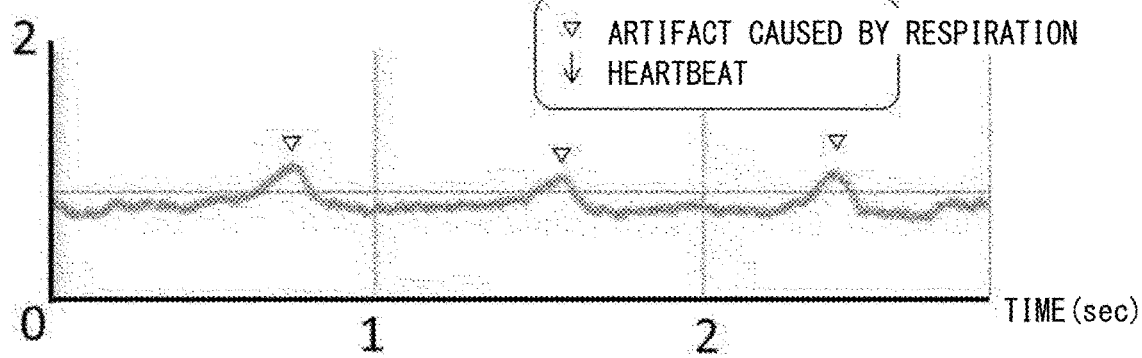
(b) IMMEDIATELY AFTER ISCHEMIA OCCURS NO PULSE DETECTED FIG. 13
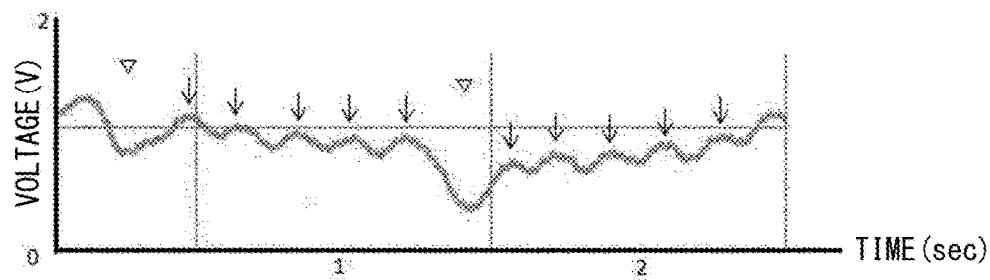
(a) IMMEDIATELY AFTER CONGESTION OCCURS PULSES DETECTED
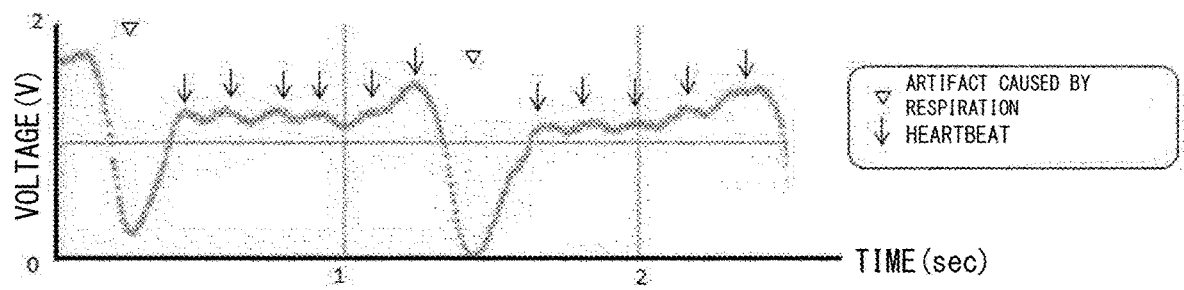
(b) 20 MINUTES AFTER CONGESTION OCCURS PULSES DETECTED
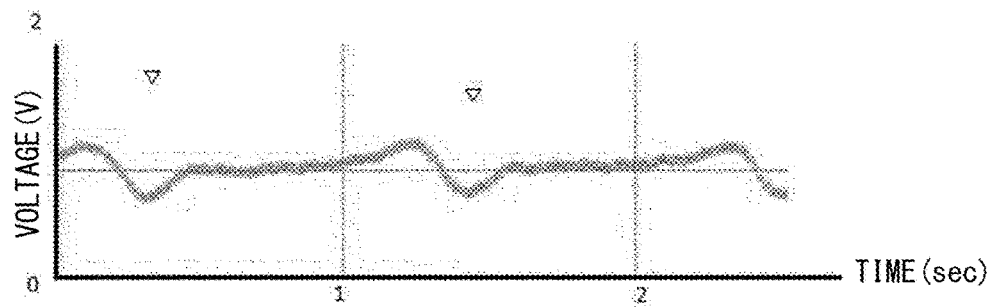
(c) 40 MINUTES AFTER CONGESTION OCCURS NO PULSE DETECTED

DEVICE FOR DETECTING BLOOD FLOW DISTURBANCE

TECHNICAL FIELD

One or more embodiments of the present invention relate to a device for detecting a blood flow disorder in a living tissue. One or more embodiments of the present invention relate to a device for detecting blood flow disorders such as congestion and ischemia. This application claims priority to Japanese Patent Application, Tokugan, No. 2015-157488, filed on Aug. 7, 2015, the disclosure of which is incorporated by reference herein in its entirety.

BACKGROUND

In breast cancer treatment by removal of a cancerous breast, reconstruction of a removed part of the breast after surgery can relieve mental distress of a patient and improve the quality of life (QOL) of the patient. The latest breast reconstruction includes plastic surgery (called plastic surgery with a free flap). In this plastic surgery, a skin/subcutaneous tissue and/or a deep tissue (called a flap) in which blood flows is cut off and taken from a region (such as an abdominal region or a back region) apart from a removed part, and then transplanted to the removed part. The flap is cut off so as to include blood vessels (arteries and veins). Then, when the flap is transplanted to the removed part, the blood vessels of the flap is sutured to blood vessels of a healthy tissue in the vicinity of the removed part, so that blood flow restarts in thus transplanted tissue and leads to engraftment of that tissue.

In this case, there is a risk that a blood flow disorder such as congestion or ischemia in the transplanted tissue may occur due to blockage of a blood vessel caused by coagulated blood as a blood clot in the transplanted tissue or due to leakage of blood from a suture portion which leakage is caused by failure in suture of the blood vessels. Delayed detection of such a disorder may result in necrosis of the transplanted tissue in the worst case. Earlier detection of a blood flow disorder and an earlier second surgery lead to an increased recovery rate of the transplanted tissue. Accordingly, after a first surgery, frequent check of a surgery site is needed. This has been a very heavy labor load in medical institutions. In addition, it is very difficult to detect an initial blood flow disorder. Therefore, the risk of a delayed second surgery always exists.

Further, in a surgery in which any of four limbs or any of fingers accidentally amputated is/are reattached, the success of the surgery depends on if blood flow in such an amputated portion can be successfully restored by suturing blood vessels of the amputated portion and blood vessels of a healthy portion closer to a trunk of the body. Also in this case, it is very important to detect a blood flow disorder early by frequent postoperative observation.

As a method, currently employed in medical practice, for identifying a blood flow disorder in a transplanted tissue, there are, for example, a refill method in which a medical staff compresses and discolors a transplanted portion and a blood flow disorder is determined by a time needed to restore the original color of the transplanted portion, a method in which a color suggesting congestion or a color suggesting ischemia is determined by visual observation, and a method for determining a blood flow disorder on the basis of a state of bleeding caused by a pinprick. Such checks need to be performed every few hours regardless of day or night for approximately one week after a surgery. Therefore, such checks have been a large burden on the medical front. Further, sufficient technical acquisition and experiences are required to determine a blood flow state by any of the above methods. Otherwise, there is a risk of making an erroneous determination. On this account, there has been a strong demand for a system for constantly monitoring a blood flow state of a transplanted portion which system does not require technical acquisition or experiences.

As conventional techniques for detecting a blood flow disorder, the following (i) to (iii) are known or disclosed: (i) a device for detecting a disorder on the basis of changes in skin color after release of compression on a skin portion in a case where blood flow is blocked by the compression on the skin portion such that the skin portion turns whitish and then the skin portion is released from the compression (Patent Literature 1); (ii) a technique for determining a blood circulation disorder at the surface of skin on the basis of an oxygen level in the blood (Patent Literature 2); and (iii) a technique for determining congestion on the basis of pulse waves with use of a congestion determining device (Patent Literature 3).

CITATION LIST

Patent Literature

[Patent Literature 1]
Published Japanese Translation of PCT International Application, Tokuhyo, No. 2002-540869
[Patent Literature 2]
Japanese Patent Application Publication, Tokukaihei, No. 10-295676
[Patent Literature 3]
Japanese Patent Application Publication, Tokukai, No. 2013-94222

SUMMARY

A skin evaluation apparatus disclosed in Patent Literature 1 evaluates a blood circulation state on the basis of a change in skin color after release from compression on skin. However, a large-scale apparatus is required for the compression of skin. Such a large-scale apparatus puts a heavy load on a patient when attached to the patient. Meanwhile, it is necessary to avoid application of excessive stress particularly to the surface of an unstable tissue, such as a transplanted tissue, when engraftment of such a tissue in a healthy tissue has not yet occurred.

A blood circulation disorder measuring device disclosed in Patent Literature 2 obtains a change in oxygen level in blood by use of light at a plurality of wavelengths in a range of 660 nm to 950 nm. However, prediction of the presence of a blood circulation disorder requires preliminarily prepared information for reference in regard to the relation between a change in oxygen level in blood and a blood circulation state. Accordingly, the blood circulation disorder measuring device is not applicable to a blood circulation disorder for which there is no reference information, as in the case of a transplanted tissue, or to a blood circulation disorder such as congestion or ischemia which cannot be determined on the basis of an oxygen level in blood.

A congestion determining device disclosed in Patent Literature 3 determines congestion by detecting pulse waves by an optical method. However, since a blood flow state in a transplanted tissue significantly changes over time after surgery, it is difficult to accurately grasp the state of a transplanted tissue only on the basis of the strength of the pulse waves.

One or more embodiments of the present invention provide a blood flow disorder detection device which can highly reliably detect blood flow disorders such as congestion and ischemia, which blood flow disorder detection device is flexible and can be attached to a three-dimensional curved surface of a living body along that surface, without putting a mechanical load on the living body.

One or more embodiments of the present invention relate to a blood flow disorder detection device for checking a blood flow state of a living tissue, the blood flow disorder detection device including: a sensor sheet including a flexible substrate and a plurality of types of sensing sections ("sensors") which measure different kinds of blood flow information of the living tissue, the plurality of types of sensing sections being provided on the flexible substrate; and an analyzing section ("analyzer") which analyzes outputs of the plurality of types of sensing sections, a blood flow disorder in the living tissue being detected on the basis of the different kinds of blood flow information (i.e., a plurality of pieces of blood flow information) from the analyzing section, the different kinds of blood flow information being obtained by attaching the sensor sheet to the living tissue.

Further, the above blood flow disorder detection device is configured, for example, such that one of the plurality of types of sensing sections measures pulse waves or heartbeats as the blood flow information.

Further, the above blood flow disorder detection device is configured, for example, such that one of the plurality of types of sensing sections measures color as the blood flow information.

Further, the above blood flow disorder detection device is configured, for example, such that one of the plurality of types of sensing sections measures temperature as the blood flow information.

Further, the above blood flow disorder detection device is configured, for example, such that the plurality of types of sensing sections includes: a first sensing section which measures pulse waves or heartbeats, the first sensing section including a light-emitting element and a light-receiving element for detecting a color specifically absorbed by blood; and a second sensing section which measures color, the second sensing section including a light-emitting element and a light-receiving element for detecting at least two different colors. Furthermore, the first sensing section may use green light whereas the second sensing section may use red light and green light.

Further, the above blood flow disorder detection device is configured, for example, such that the sensor sheet is made of a laminate including a transparent adhesive layer which is used to attach the sensor sheet to a living body.

Further, the above blood flow disorder detection device is configured, for example, such that the sensor sheet is at least partially transparent and allows for observation of color of the living tissue even in a state in which the sensor sheet is attached to the living tissue.

Further, the above blood flow disorder detection device is configured, for example, such that: at least one of the plurality of sensing sections measures the blood flow information at a reference point of the living tissue; and the analyzing section detects the blood flow disorder in the living tissue with reference to the blood flow information at the reference point.

Note that two or more of the above features according to one or more embodiments of the present invention can be arbitrarily combined in a single embodiment.

One or more embodiments of the present invention make it possible to provide a blood flow disorder detection device which can highly reliably detect blood flow disorders such as congestion and ischemia, which blood flow disorder detection device is flexible and can be attached to a three-dimensional curved surface of a living body along that surface, without putting a mechanical load on a living tissue. Further, since the living tissue can be visually observed even when the blood flow disorder detection device is being attached to the living body, it is possible to provide a blood flow disorder detection device capable of avoiding an unexpected risk and performing checks on various aspects. Further, a subject to whom the blood flow disorder detection device is applied can carry out activities while the blood flow disorder detection device is attached to the subject. This means that it is possible to provide a blood flow disorder detection device which puts a less load to a subject to whom the blood flow disorder detection device is applied.

BRIEF DESCRIPTION OF DRAWINGS

FIG. 12 is a chart showing an output of a blood flow sensor in ischemia in accordance with one or more embodiments of the present invention, as shown in Examples.

FIG. 13 is a chart showing an output of a blood flow sensor in congestion in accordance with one or more embodiments of the present invention, as shown in Examples.

DETAILED DESCRIPTION OF EMBODIMENTS

The following will discuss a configuration of a blood flow disorder detection device according to one or more embodiments of the present invention, with reference to drawings. For convenience, the drawings to which the following description refers may show an enlarged view of a portion that is a feature according to one or more embodiments of the present invention. This is intended for easy understanding of the feature according to one or more embodiments of the present invention. Accordingly, the drawings do not always show a real dimensional ratio of constituent elements, and the like. Materials, dimensions, etc. described below are each merely an example. Accordingly, the present invention is not limited to such materials, dimensions, etc. and the materials, dimensions, etc. can be changed as appropriate within the scope of the present invention.

Figure 1:
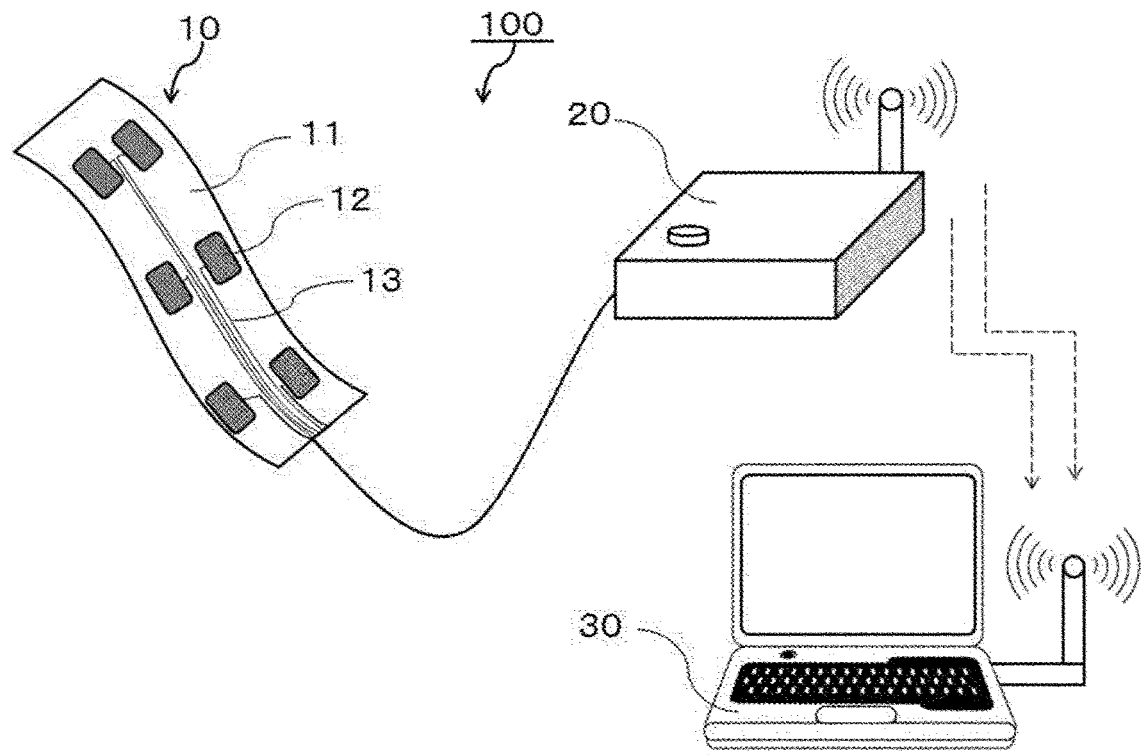
FIG. 1 is a view schematically illustrating a configuration of a blood flow disorder detection device in accordance with one or more embodiments of the present invention.
Figure 2A:
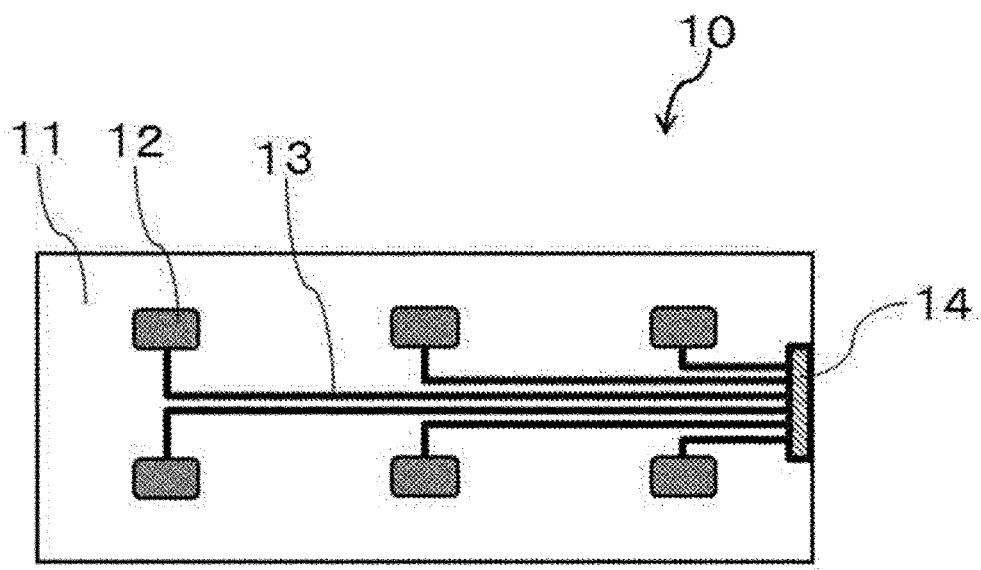
FIG. 2A is a plan view schematically illustrating a planar configuration of a sensor sheet in accordance with one or more embodiments of the present invention.
Figure 2B:
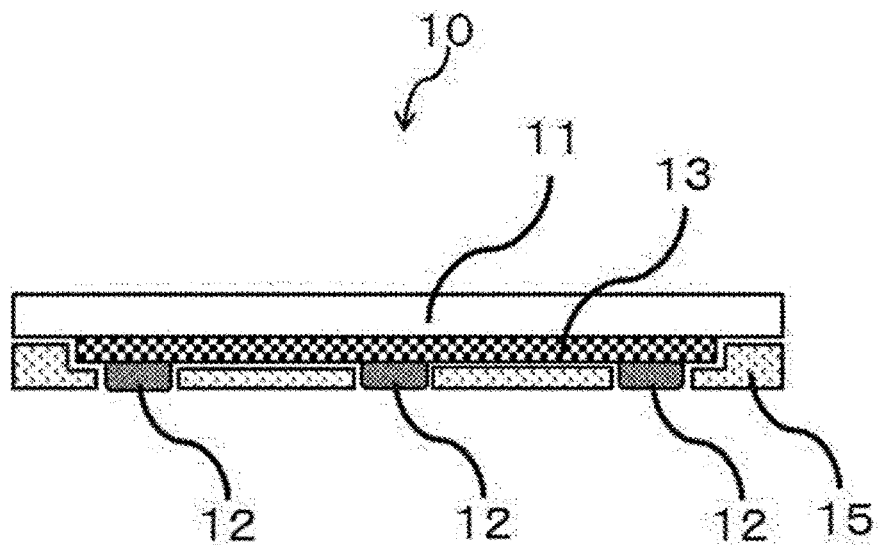
FIG. 2B is a cross sectional view schematically illustrating a configuration of the sensor sheet in accordance with one or more embodiments of the present invention.

FIG. 1 is a view schematically illustrating a blood flow disorder detection device in accordance with one or more embodiments of the present invention. FIG. 2A is a plan view schematically illustrating a planar configuration of a sensor sheet of the blood flow disorder detection device. FIG. 2B is a cross sectional view schematically illustrating the configuration of the sensor sheet of the blood flow disorder detection device.

A blood flow disorder detection device 100 in accordance with one or more embodiments of the present invention include a sensor sheet 10, a control device 20 for controlling the sensor sheet, and a computer 30 for analyzing measurement outputs of sensors. The sensor sheet 10 is arranged such that a plurality of reflective optical sensors 12 as sensing means is mounted on a flexible thin substrate 11. Further, on this substrate 11, wiring lines 13 are provided. The wiring lines 13 serve as power lines for supplying power to the optical sensors 12 and as signal lines for reading out sensor outputs.

The wiring lines 13 connected to the optical sensors 12 are arranged such that the wiring lines 13 extend toward one end of the substrate 11 and concentrated at a terminal part 14. The terminal part 14 connects the sensor sheet 10 to the control device 20 at one end of the sensor sheet 10 that is configured in a band form. Further, since the sensor sheet 10, when used, is attached to a living tissue that is a target of measurement, an adhesive layer 15 is provided on a surface of the substrate 11 on which surface the optical sensors 12 are mounted. This adhesive layer 15 serves as means for fixing the sensor sheet 10 to the living tissue. The adhesive layer 15 is provided with open windows at positions corresponding to respective positions of the optical sensors 12. This adhesive layer 15 also functions as a spacer keeping an appropriate distance between the optical sensors 12 and a surface that is a target of measurement. Alternatively, the adhesive layer 15 is configured to have depressed areas at respective positions where the optical sensors 12 are provided, and to seal an attachment surface of the sensor sheet 10. Such a configuration is effective for washing/sterilizing treatment of the sensor sheet 10, prevention of bacteria adhesion to the sensor sheet 10, and prevention of damage to a living body by any of the optical sensors 12 that are hard.

The control device 20 is connected via a cable to the sensor sheet 10. The control device 20 has, as functions to control the optical sensors 12 on the sensor sheet 10, the following functions: a function to supply power to the sensors 12; a function to drive the sensors 12; a function to process a signal of a sensor output; and a wireless communication function for providing/receiving data to/from the computer. The computer 30 is connected by wireless communication with the control device 20. The computer 30 thereby exchanges, with the control device 20, control information for the optical sensors 12, and provides/receives, to/from the control device 20, output data of the optical sensors 12. The computer 30 accumulates the control information and the output data. On the basis of the output data obtained from the sensors, the computer 30 as analyzing means extracts blood flow information of the living tissue that is a target of measurement, and determines the presence of a blood flow disorder in the living tissue and a degree of the blood flow disorder. Pieces of such blood flow information are transmitted to a central monitoring system by communication means (not illustrated). Then, an alarm for notifying an abnormality is generated as necessary.

Next, the following will discuss in detail sensing means in the blood flow disorder detection device in accordance with one or more embodiments of the present invention.

Figure 3:
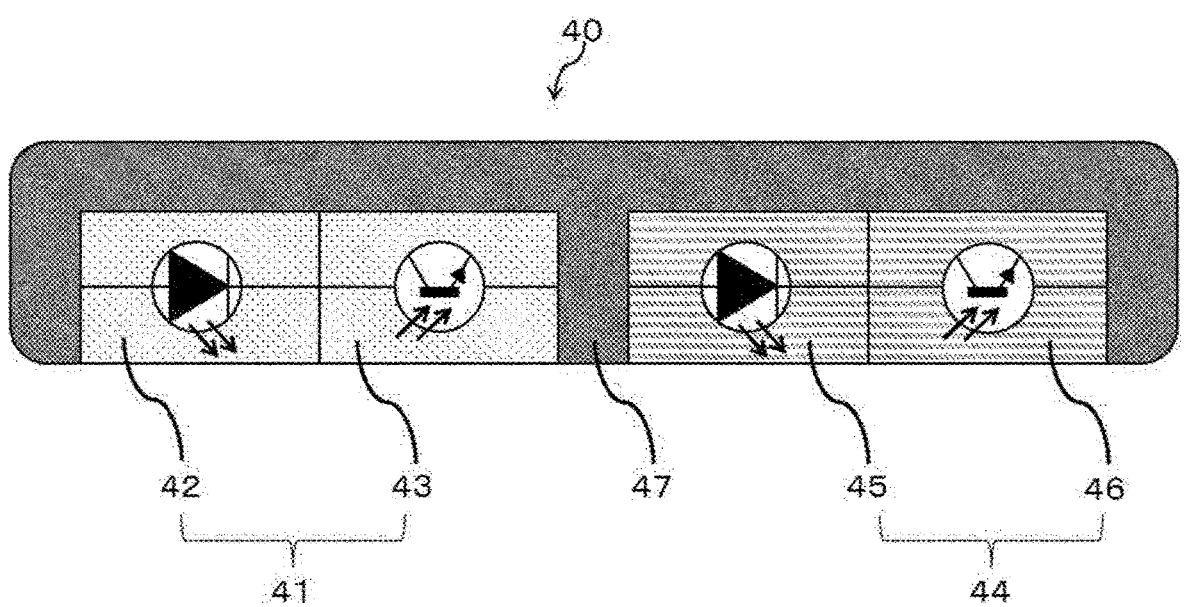
FIG. 3 is a view schematically illustrating a cross section of an optical sensor in accordance with one or more embodiments of the present invention.

FIG. 3 is a view schematically illustrating a cross sectional configuration of an optical sensor serving as sensing means in accordance with one or more embodiments of the present invention. An optical sensor 40 is configured by incorporating two reflective optical sensor elements 41 and 44 in a package 47. The package 47 has a rectangular parallelepiped shape. At a lower surface of the package 47, a light-emitting surface and a light-receiving surface of each of the optical sensor elements 41 and 44 are provided. Further, the package 47 is provided with wiring terminals (not illustrated) for supply of driving power and for reading an output of each of the optical sensor elements 41 and 44. These wiring terminals are connected to the wiring lines 13. The reflective optical sensor element 41 is made of a combination of a light-emitting element 42 and a light-receiving element 43, and the reflective optical sensor 44 is made of a combination of a light-emitting element and a light-receiving element 46. When light is emitted from the light-emitting elements 42 and 45 toward an object to be measured, reflected light from the object to be measured is detected by each of the light-receiving elements 43 and 46. Then, properties of the object to be measured are measured on the basis of intensity of the reflected light and a change in the intensity of the reflected light over time.

In the present embodiment, the light-emitting elements 42 and 45 are light-emitting diodes, and the light-receiving elements 43 and 46 are made of photo transistors. The light emitted from the light-emitting element 42 has an optical spectrum of green light which is of a color specifically absorbed by blood. Meanwhile, the light emitted from the light-emitting element 45 has an optical spectrum of red light. After the light with which a living tissue as an object to be measured is irradiated enters the living tissue, the light is transmitted, absorbed, and reflected in each of arterial blood, venous blood, and the living tissue. Thereafter, backscattered light of that light is received by the light-receiving elements. Though a substantially constant amount of light is absorbed by venous blood and the living tissue, an amount of light absorbed by arterial blood varies depending on an arterial blood amount in a living body since the arterial blood amount increases/decreases in accordance with pulsation associated with heartbeats. On this account, backscattered light of the light absorbed by arterial blood varies in synchronization with pulsation. Therefore, pulse waves or heartbeats can be electrically measured by detecting the backscattered light from arterial blood by use of the light-receiving element and then further detecting a pulsation component by use of the computer 30.

Light absorption by blood is mainly absorption by hemoglobin. Hemoglobin specifically absorbs green light at wavelengths in a range of about 520 nm to 580 nm. Accordingly, in the sensing means for measurement of pulse waves or heartbeats of blood flow, the optical sensor element 41 employs, as a light source, the light-emitting element 42 that emits green light.

On the other hand, in a case where a change in color of an object to be measured is to be detected, the change in color is a change in spectrum of reflected light. Accordingly, in a minimum configuration, two different colors need to be detected. In a case where a histological abnormality associated with blood flow in a living tissue as an object to be measured is to be detected, it is important to catch a change in color related to blood, and a change in color related to pigment, such as melamine, of an upper layer tissue of a flap. As described above, in order to catch a change in color related to blood which change is caused by hemoglobin, light mainly including green light in a range of about 520 nm to 570 nm is suitably used since the green light is specifically absorbed by blood. On the other hand, light suitable for catching a change in color related to pigment is light of a color which hemoglobin less absorbs. Specifically, such light is light mainly including red light in a range of about 600 nm to 800 nm. In view of the above, the present embodiment employs the light-emitting element 45, which emits red light that is relatively less absorbed by hemoglobin, as a source of light for use in the sensing means for color measurement. This is intended to catch a change in absorption of pigment by an upper layer tissue of a flap.

Further, in a case where a histological abnormality associated with blood flow in a living tissue as an object to be measured is to be detected, use of light of a color which is specifically-absorbed by blood is suitable for detection of a change in color related to blood. For this purpose, as described above, use of a green light source is suitable as with the case of the sensing means for blood flow measurement. In other words, one optical sensor for measurement with use of green light can be used both as an optical sensor for measurement of pulse waves or heartbeats of blood flow and as an optical sensor for detecting, on the basis of color, a blood flow abnormality in a living tissue. Therefore, in the present embodiment, the optical sensor element 41 using green light is used in the sensing means for measurement of pulse waves or heartbeats of blood flow in a living tissue, while the optical sensor element 41 using green light and the optical sensor element 44 using red light are used in the sensing means for color measurement of a living tissue. The above configuration makes it possible to measure both a color and pulse waves or heartbeats of blood flow at one position of a living tissue. This accordingly makes it possible to accurately and precisely detect a blood flow disorder by analyzing a blood flow disorder in a living tissue from various aspects.

Figure 4:
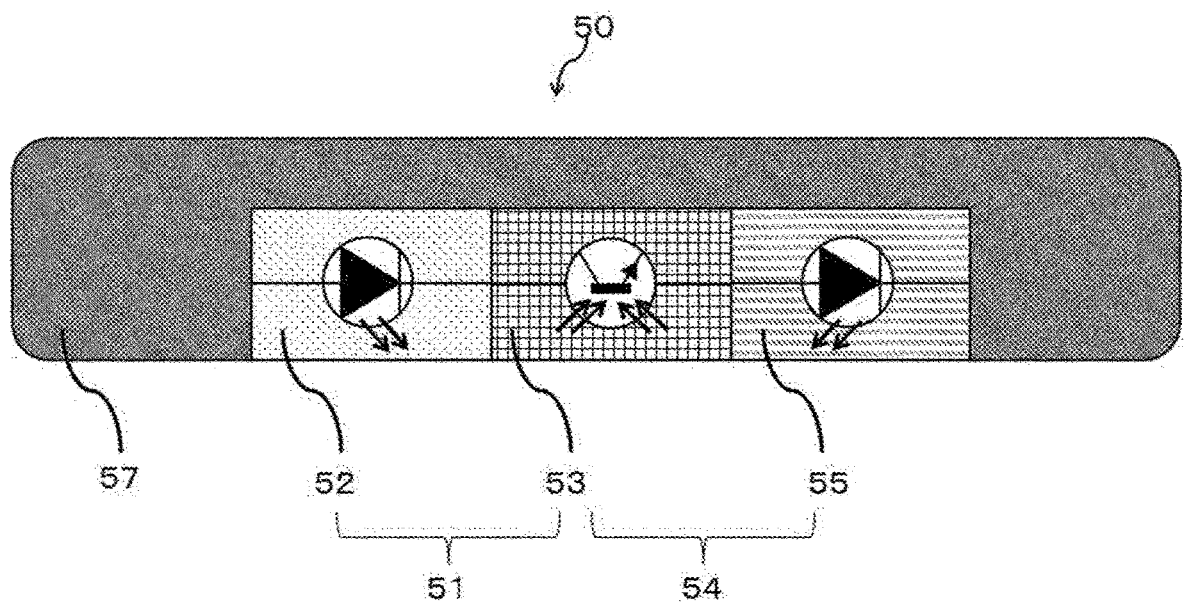
FIG. 4 is a view schematically illustrating a cross section of an optical sensor in accordance with one or more embodiments of the present invention.

FIG. 4 is a view schematically illustrating a cross sectional configuration of an optical sensor serving as sensing means in accordance with one or more embodiments of the present invention. An optical sensor 50 is configured by incorporating two reflective optical sensor elements 51 and 54 sharing a light-receiving element 53 in a package 57. The package 57 has a rectangular parallelepiped shape. At a lower surface of the package 57, a light-emitting surface and a light-receiving surface of each of the optical sensor elements 51 and 54 are provided. Further, the package 57 is provided with wiring terminals (not illustrated) for supply of driving power and for reading an output of each of the optical sensor elements 51 and 54. These wiring terminals are connected to the wiring lines 13. The light-emitting element 52 constituting the reflective optical sensor element 51 is a light-emitting diode which emits green light that is of a color specifically absorbed by blood. The light-emitting element 55 constituting the reflective optical sensor element 54 is a light-emitting diode which emits red light which is of a color that is less absorbed by blood. The light-receiving element 53 is a photodiode and can detect light of colors ranging from green to red.

In the present embodiment, the optical sensor element 51 using green light is used in the sensing means for measurement of pulse waves or heartbeats of blood flow in a living tissue while the optical sensor element 51 using green light and the optical sensor element 54 using red light are used in the sensing means for color measurement of a living tissue, as in the above embodiment illustrated in FIG. 3. In the present embodiment, the optical sensor element 51 using green light is used not only for measurement of pulse waves or heartbeats but also for color measurement. In addition, the light-receiving element 53 is also used for both of measurement of pulse waves or heartbeats and color measurement. This makes it possible to reduce the number of wiring lines 13 in the sensor sheet 10. This reduction in the number of wiring lines makes it possible to mount a large number of optical sensor elements on a sensor sheet. However, since the light-receiving element 53 is shared by the optical sensor elements 51 and 54, the optical sensor elements 51 and 54 cannot carry out measurement at the same time. Therefore, the control device 20 carries out control such that the light-emitting elements 52 and 55 are subjected to time-sharing driving and that in synchronization with the time-sharing driving, outputs of the light-receiving element 53 are distinguished into either green information or red information.

Figure 5:
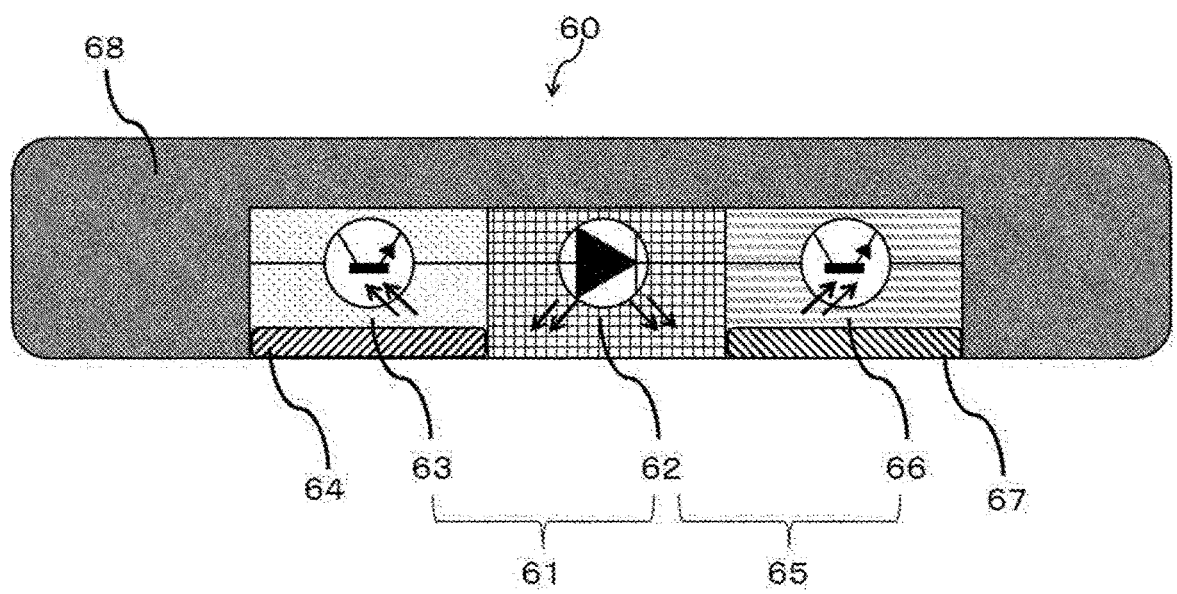
FIG. 5 is a view schematically illustrating a cross section of an optical sensor in accordance with one or more embodiments of the present invention.

FIG. 5 is a view schematically illustrating a cross sectional configuration of an optical sensor serving as sensing means in accordance with one or more embodiments of the present invention. An optical sensor 60 is configured by incorporating two reflective optical sensor elements 61 and 65 sharing a light-emitting element 62 in a package 68. The package 68 has a rectangular parallelepiped shape. At a lower surface of the package 68, a light-emitting surface and a light-receiving surface of each of the optical sensor elements 61 and 65 are provided. Further, the package 68 is provided with wiring terminals (not illustrated) for supply of driving power and for reading an output of each of the optical sensor elements 61 and 65. These wiring terminals are connected to the wiring lines 13. The reflective optical sensor element 61 includes a light-emitting element 63. This light emitting element 63 is a phototransistor incorporating a color filter 64 selectively transmitting green light which is of a color that is specifically absorbed by blood. The light-emitting element 66 constituting the reflective optical sensor element 65 is a phototransistor incorporating a color filter 67 selectively transmitting red light which is of a color that is less absorbed by blood. The light-emitting element 62 shared by the above two optical sensors is a light-emitting diode emitting light whose components are at wavelengths in a range of green to red. The light-emitting element 62 can be, for example, a white light-emitting diode.

In the present embodiment, the optical sensor element 61 using green light is used in the sensing means for measurement of pulse waves or heartbeats in a living tissue while the optical sensor element 61 using green light and the optical sensor element 65 using red light are used in the sensing means for color measurement of a living tissue, as in the above embodiment illustrated in FIG. 3. In the present embodiment, the optical sensor element 61 using green light is used not only for measurement of pulse waves or heartbeats but also for color measurement. In addition, the light-emitting element 62 is also used for both measurement of pulse waves or heartbeats and color measurement. This makes it possible to reduce the number of wiring lines 13 in the sensor sheet 10, as in the above embodiment illustrated in FIG. 4. This reduction in the number of wiring lines makes it possible to mount a large number of optical sensor elements on a sensor sheet. Meanwhile, unlike the embodiment illustrated in FIG. 4, the present embodiment allows the optical sensor elements 61 and 65 to carry out measurement at the same time.

Figure 6:
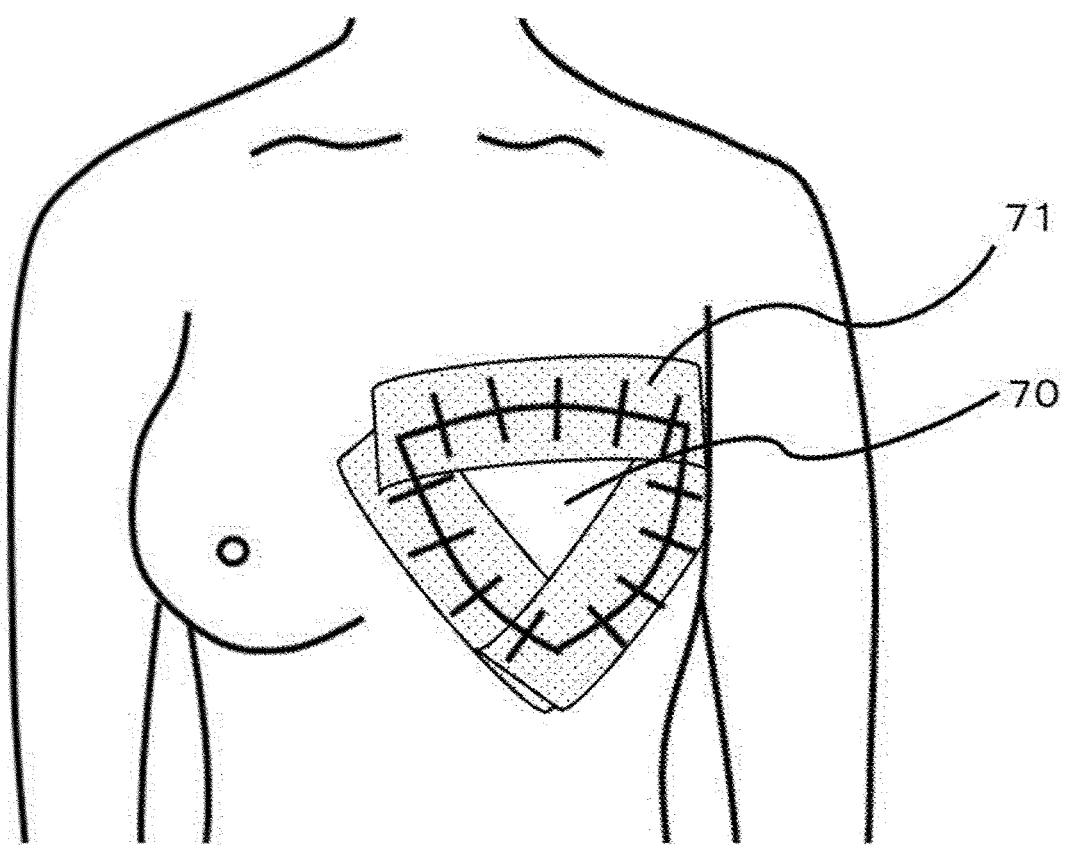
FIG. 6 is a view illustrating a transplanted living tissue to which a device according to one or more embodiments of the present invention is applied.

Next, the following will discuss an example, in which a blood flow disorder detection device in accordance with one or more embodiments of the present invention is applied to a transplanted tissue in order to detect a blood flow disorder. FIG. 6 illustrates reconstruction of a removed part of a breast after surgical removal of the breast that has become cancerous. In FIG. 6, a flap 70 including skin, a subcutaneous tissue, and/or a deep tissue which have been cut off from a patient is transplanted to the removed part of the breast, and blood vessels, the skin, and/or the subcutaneous tissue are surgically sutured to those of a healthy tissue in the vicinity of the removed part. For prevention of infectious diseases and for prevention of drying and/or mechanical damage of a suture site, a protective tape 71 is attached to a suture portion of a transplanted tissue. In one or more embodiments of the present invention, in order to detect a blood flow disorder at the suture portion as a main observation point, the protective tape 71 may be transparent to light at wavelengths in a range of a spectrum of light for use in measurement. Such a protective tape can be, for example, a laminate of a transparent polyethylene film and a transparent adhesive, such as a silicone adhesive or an acrylic adhesive, which is provided on the transparent polyethylene film.

Figure 7:
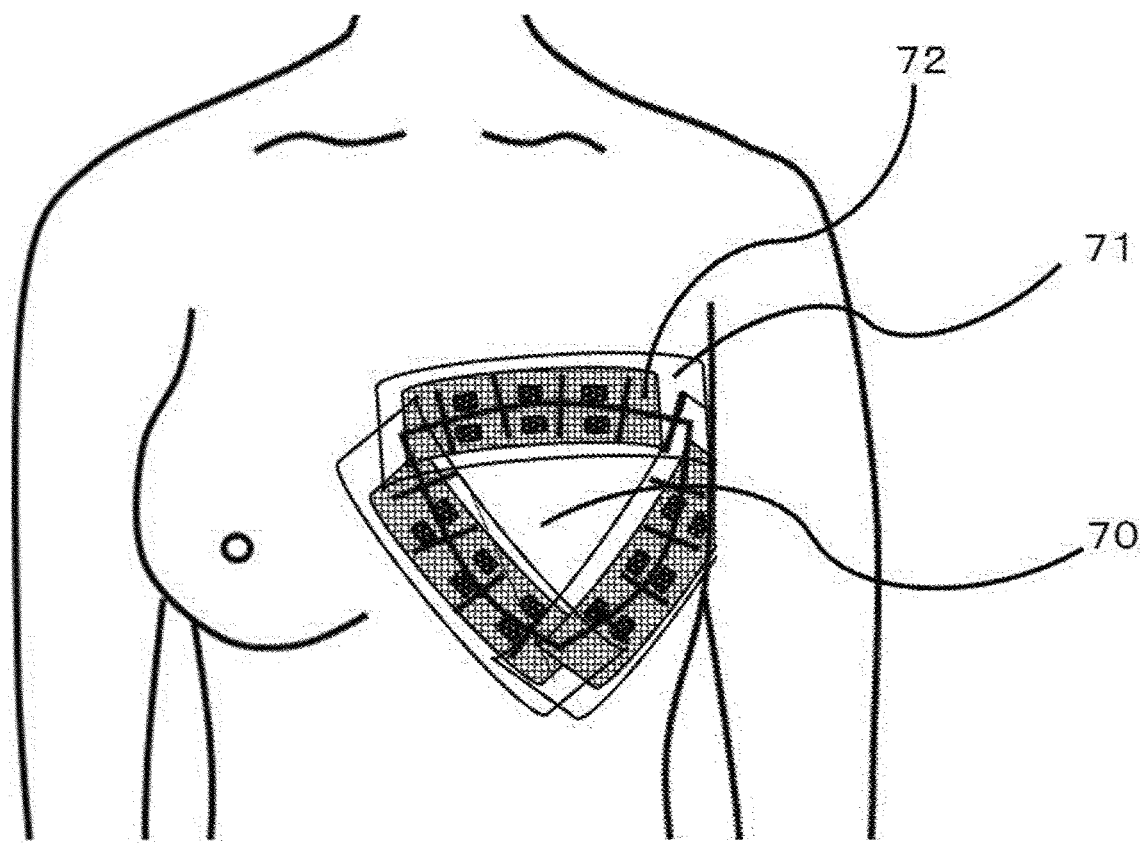
FIG. 7 is a view illustrating a case where a blood flow disorder device in accordance with one or more embodiments of the present invention is applied to a transplanted living tissue.
Figure 8:
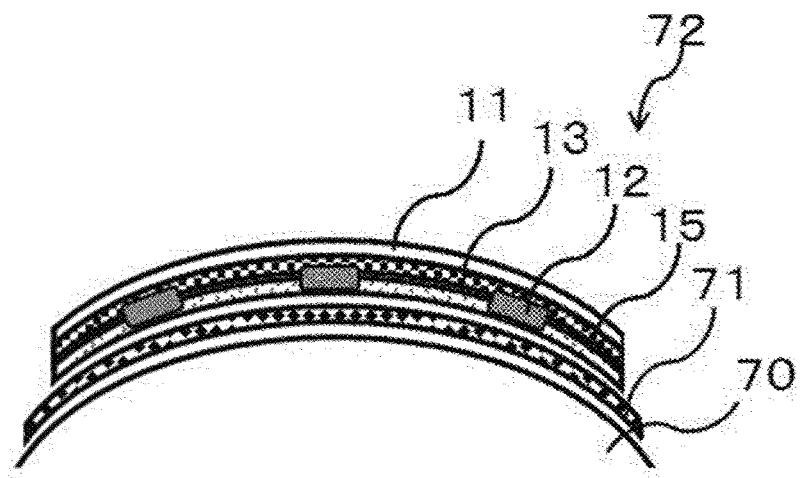
FIG. 8 is a cross-sectional view illustrating a case where a blood flow disorder device in accordance with one or more embodiments of the present invention is applied to a transplanted living tissue.

As illustrated in FIG. 7, a sensor sheet 72 as illustrated in FIGS. 2A and 2B is fixed with the adhesive layer 15 onto pieces of such a protective tape 70. In this case, some of optical sensor elements of the sensor sheet are arranged to be present on skin of a healthy tissue portion beyond the suture portion. Information from these optical sensor elements provided on the healthy tissue portion is used, by the computer 30 as analyzing means, as a reference for determination of a blood flow state in a transplanted portion. FIG. 8 illustrates a cross section of the sensor sheet attached to a flap. In the present embodiment, a laminated structure of the protective tape 71 and the sensor sheet 72 allows a patient to easily detach the sensor sheet at the time when patient takes a bath. Further, the sensor sheet 72 is fixed onto the protective tape 71 with an adhesive layer such that a distance between skin and the optical sensor elements are kept constant. The adhesive layer is a transparent adhesive layer made of a silicone material (Polydimethylsilocane (PDMS)) and provided on an attachment surface of the sensor sheet 72.

Figure 9:
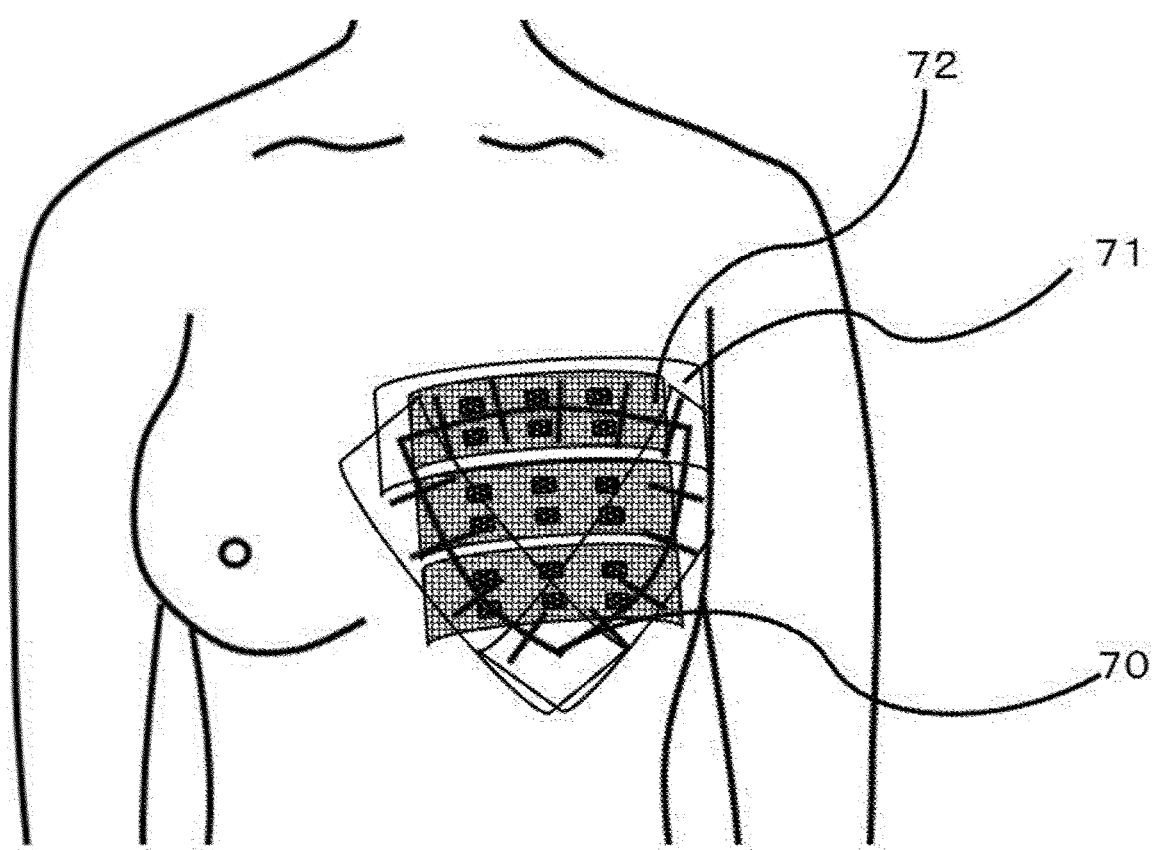
FIG. 9 is a view illustrating a case where a blood flow disorder device in accordance with one or more embodiments of the present invention is applied to a transplanted living tissue.

FIG. 9 illustrates another method of attaching the sensor sheet 72 in accordance with one or more embodiments of the present invention. The sensor sheet 72 is in the form of narrow tape. Accordingly, the sensor sheet 72 can be adhered to a three-dimensional curved surface of a living body along that surface so as to be in contact with the surface. Further, in the embodiments illustrated in FIGS. 7 and 9, the control device 20 (not illustrated) is fixed, by using a belt or tape, to an upper arm portion or a surface of a healthy portion that is not a transplanted portion. Then, the control device 20 and the terminal part 14 of the sensor sheet 72 are connected to each other via a cable.

Figure 10:
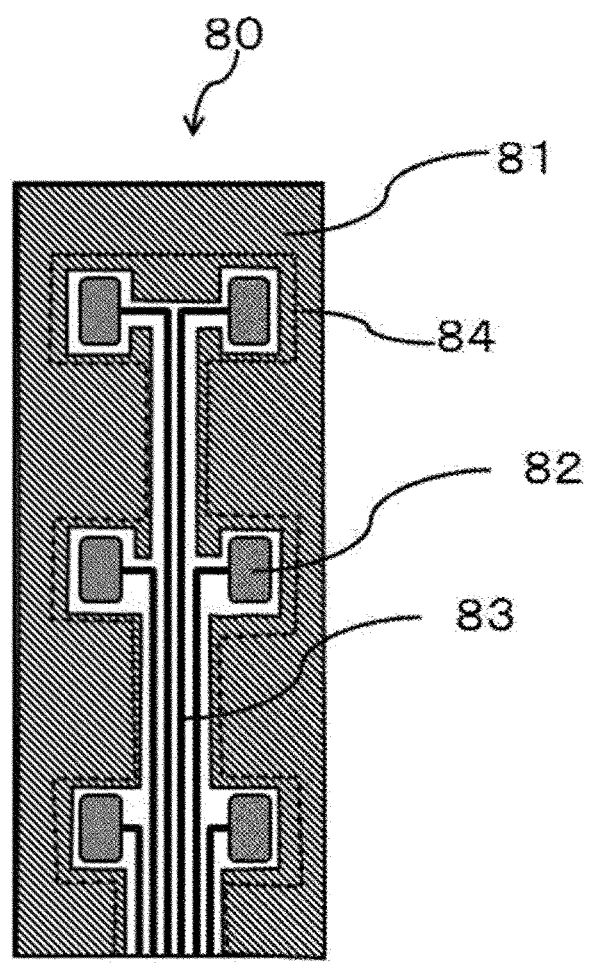
FIG. 10 is a plan view schematically illustrating a planar configuration of a sensor sheet in accordance with one or more embodiments of the present invention.

The blood flow disorder detection device in accordance with one or more embodiments of the present invention is very useful for detection of a blood flow disorder in a transplanted tissue after tissue transplantation. However, visual observation by doctors and medical staffs is also important for avoiding unexpected abnormal changes. Easy visual observation has not been sufficiently considered in conventional devices. In view of the above, in one or more embodiments of the present invention, an optical sensor portion 82 of a sensor sheet 80 is shielded from light by black paint or aluminum film, as illustrated in FIG. 10, so that noise caused by external light will be prevented. Meanwhile, a substrate and an adhesive layer of the sensor sheet are each made of a transparent material so that other portions 81, which exclude the sensor portion 82, will be transparent. Further, on a substrate surface on an opposite side of the other substrate surface where the sensor portion of the sensor sheet 80 is provided, a non-transparent device portion 84 (on an inner side of dotted line) including the optical sensor portion 82 and a wiring portion 83 is masked so as to be a color similar to that of skin. Such masking reduces contrast of color and/or luminance between the device and the skin. This makes it possible to prevent a different color when a skin color is seen through the device.

EXAMPLES

The following will discuss in detail Examples according to one or more embodiments of the present invention. In Examples, animal experiments using rats are employed to produce congestion and ischemia that are the same as those in actual conditions in which a blood flow disorder occurs. Applicability of such experiments to human beings is shown in methodology of animal experiments. Embodiments of the present invention are not limited to the following Examples.
(Optical Sensor for Measurement of Pulse Waves or Heartbeats)

As an optical sensor for measurement of pulse waves or heartbeats, an optical sensor (product number: NJL5303R_J) manufactured by New Japan Radio Co., Ltd. was used. This optical sensor is a photo reflector including a light-emitting diode emitting green light having a peak at a wavelength of 570 nm and a phototransistor having a light-receiving sensitivity peak at wavelengths of a green color. The optical sensor can be suitably used for measurement with use of reflected light.
(Optical Sensor for Color Measurement)

As an optical sensor for color measurement, a digital color sensor (Hamamatsu Photonics K.K.: 59706) was used. The sensitivity of this digital color sensor can be adjusted by changing a time of exposure. The digital color sensor includes sensors sensitive to respective color components of red (center wavelength: 615 nm), green (center wavelength: 540 nm), and blue (center wavelength: 465 nm). The digital color sensor outputs digital values of 256 levels in the order of red, green, and blue. Further, a white light-emitting diode was used as a light source for color measurement.

(Sensor Sheet)

A flexible and highly biocompatible silicone material (Polydimethylsilocane (PDMS)) having a thickness of 1 mm was provided with depressed areas at constant intervals. The above optical sensors for measurement of pulse waves or heartbeats and the above optical sensors for color measurement were embedded and fixed in the depressed areas. This allows an attachment surface of a sensor sheet to be sealed by an adhesive layer made of PDMS. In the sensor sheet for optical sensors for measurement of blood flow, 6 sensors were provided at points arranged in 2 rows and 3 columns. The sensor sheet was connected by wiring to a control device 20.

(Control of Sensor)

The heart rate of Wister rats, which were used in the present animal experiments, is 250 times per minute to 450 times per minute. That is, a frequency of heartbeats is 4.1 Hz to 7.5 Hz. For the purpose of precise processing of sensor outputs at the above frequencies that are focused, a highpass filter circuit and a lowpass filter circuit each for noise removal were incorporated in the control device 20. Such processing can be performed by software on a computer as analyzing means. Control of the optical sensors for measurement of pulse waves or heartbeats and the optical sensors for color measurement was configured by use of a battery-driven microprocessor board in which both an input/output function and a wireless communication function were incorporated. Since a change in output voltage due to an amount of light received by each optical sensor for measurement of pulse waves or heartbeats is minute, the output voltage is amplified in the control device 20 so as to be at a level in a range of 0 V to 5 V. Thereafter, the output voltage thus amplified is subjected to analog/digital conversion. Then, the output voltage in the form of digital data is sent to the computer every 5 milliseconds by wireless communication. The computer stored thus received values as numerical data, and allows the values to be displayed in a waveform. Similarly, an output voltage of the optical sensor for color measurement is sent to the computer. The time of exposure was adjusted such that a value of a red component was at or around the center of the 256 levels. In the present Examples, the optical sensor for measurement of pulse waves or heartbeats and the optical sensor for color measurement were separately configured. Accordingly, these sensors were alternately operated in a time-sharing manner so that crosstalk due to light-emitting elements used by these sensors can be prevented.

(Blood Flow Disorder Model)

In the present animal experiments, Wister rats were used. Flaps were cut off from a left inguinal region and a right inguinal region, respectively, such that a size of each of the flaps was 3 cm by 4 cm. Then, the flaps were transplanted such that each of the flaps was joined only with aorta and vena cava in or in the vicinity of an area between a body trunk and a root portion of a leg. Since the flaps cut off are shrunken, the periphery of each of the flaps was sutured so as to be restored to a state prior to cutting as much as possible.

Figure 11:
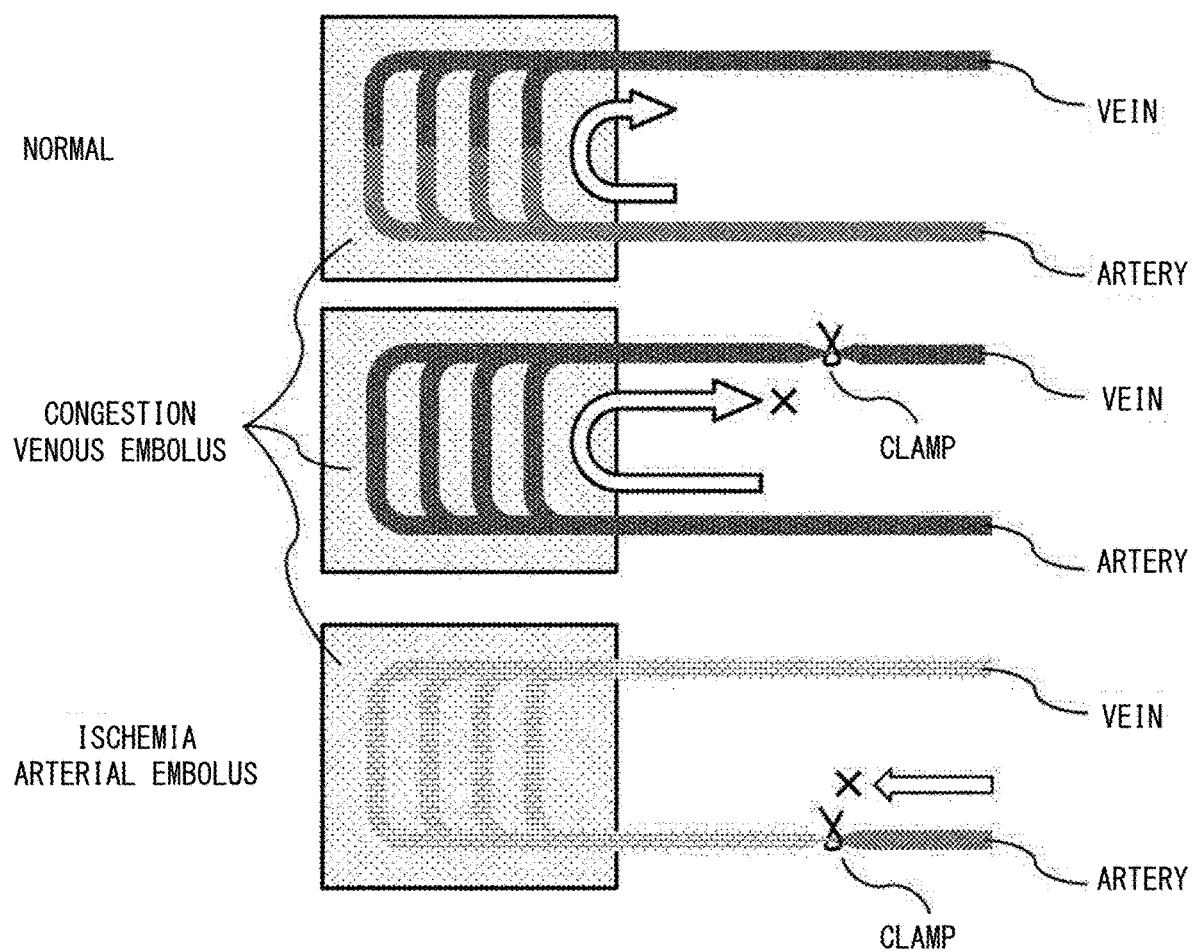
FIG. 11 is a view illustrating blood flow disorder models in accordance with one or more embodiments of the present invention, as shown in Examples.

As illustrated in FIG. 11, a congestion model and an ischemia model were evaluated as blood flow disorder models. In the congestion model, a venous embolus was caused and evaluated by clamping and blocking a vein as illustrated in FIG. 11 in the flap transplanted. Meanwhile, in the ischemia model, an arterial embolus was caused and evaluated by clamping and blocking an artery as illustrated in FIG. 11 in the flap transplanted. In order to compare an abnormal blood flow state and a normal blood flow state, only one of the flaps prepared on left and right sides was clamped and the other one of the flaps was used as a reference.

(Attachment of Optical Sensors)

To each of the flaps on the left and right sides, a protective tape was attached so as to extend on a healthy portion. Then, the optical sensors for measurement of pulse waves or heartbeats (attached on a body center side) and the optical sensors for color measurement (attached to one position on each of both outer sides relative to the optical sensors for measurement of pulse waves or heartbeats) were attached together on the protective tape. One optical sensor at an end of the sensor sheet for measurement of pulse waves or heartbeats is located on a healthy portion and arranged to be able to carry out measurement of a reference of each sensor sheet.

(Results of Evaluation)

FIG. 12 shows an output of the optical sensor for blood flow measurement before and after the artery was blocked in the ischemia model. As shown in FIG. 12(a), before the artery is blocked, the optical sensor for measurement of pulse waves or heartbeats detects pulses corresponding to heartbeats. Therefore, blood flow in the flap is measured. On the other hand, in regard to an ischemia state in which the artery is blocked, pulses corresponding to heartbeats cease to be detected immediately after the artery is blocked. This showed that in the present Example, the optical sensor for measurement of pulse waves or heartbeats works in the case of complete ischemia.

FIG. 13 shows an output of the optical sensor for measurement of pulse waves or heartbeats after the vein was blocked in the congestion model. As shown in (a) of FIG. 13, no difference in waveform is found between the congestion model right after blocking of the vein and a normal state shown in FIG. 12(a). Furthermore, in the waveform obtained 20 minutes after blocking of the vein, pulses corresponding to heartbeats are still observed as shown in FIG. 13(b). This indicates that congestion cannot be detected immediately only on the basis of the presence of pulses and/or the strength of the pulses. FIG. 13(c) shows a waveform obtained at the time when 40 minutes have elapsed after blocking of the vein. It is clear from FIG. 13(c) that, when 40 minutes had elapsed after blocking of the vein, the congestion model reached a state in which a blood flow abnormality could be detected from the waveform.

Figure 14:
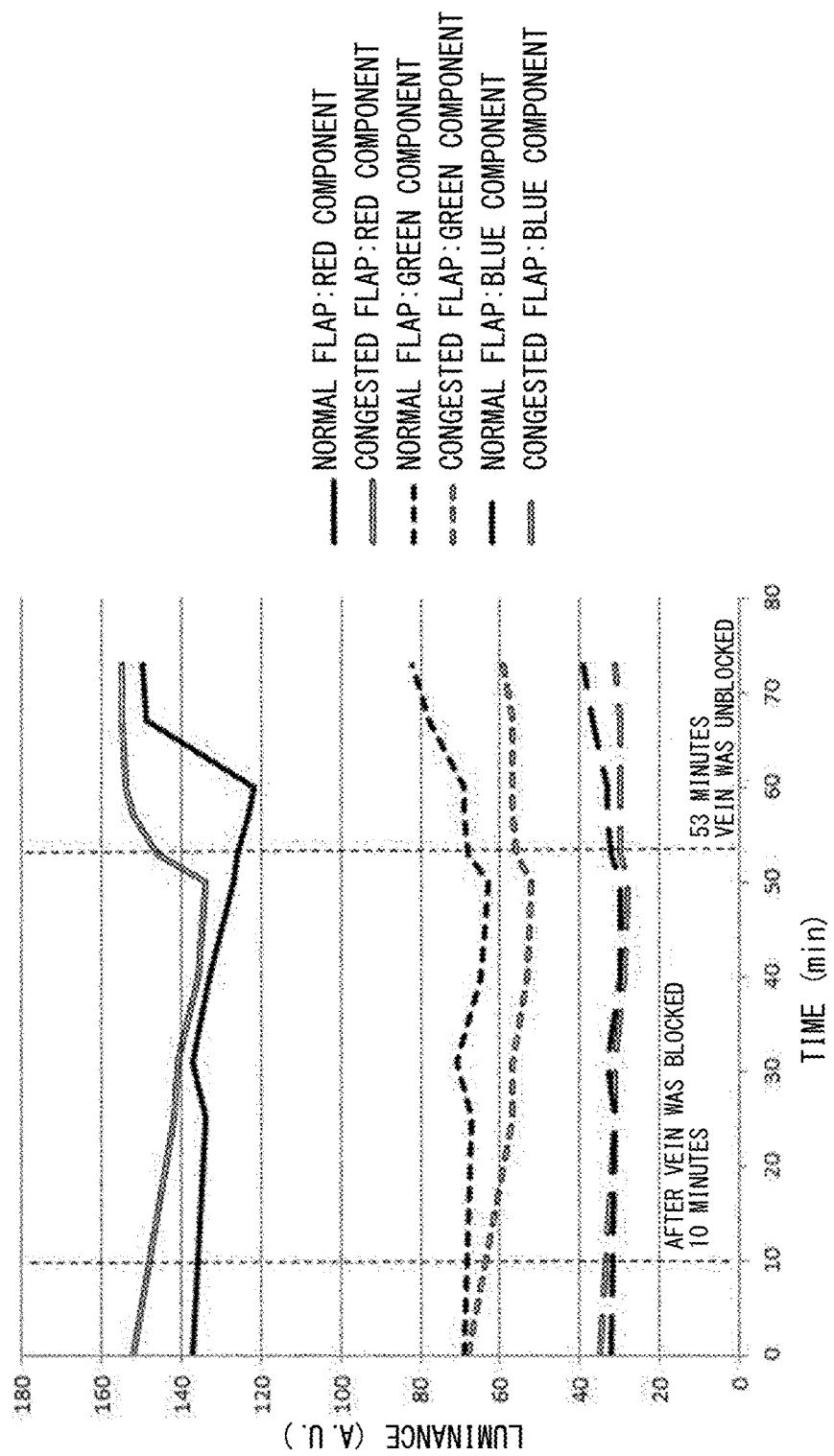
FIG. 14 is a chart showing an output of a color sensor in congestion in accordance with one or more embodiments of the present invention, as shown in Examples.

On the other hand, FIG. 14 shows an output of the optical sensor for color measurement. Subsequent to the occurrence of congestion caused by blocking of the vein, outputs of a red component and a green component have started to decrease in comparison with those of a normal flap as a reference. However, no change was observed in output of a blue component. When the vein was unblocked 53 minutes after the start of the blocking of the vein, the output of the red component of a congested flap immediately increased. Meanwhile, the output of the red component of the normal flap also decreased after 30 minutes from the start of the blocking of the vein. Then, after approximately 10 minutes from unblocking of the vein, the output of the red component of the normal flap increased as with the congested flap. This indicates that blocking of the vein changes a blood flow state of a whole mouse body and that the healthy portion is affected by such a change so as to have an induced change in tissue color.

In the case of congestion, the venous blood cannot flow out of the flap due to the blocking of the vein, so that the blood having flown into the flap from the artery is accumulated inside the flap. Accordingly, the pressure inside blood vessels in the flap increases. When the blood pressure exceeds a certain level, blood flow stops. In other words, in the case of congestion, blood flows into the flap to fill inside the flap until it becomes not possible to measure a pulse waveform. Accordingly, the optical sensor for measurement of pulse waves or heartbeats takes time to detect a congestion state.

The above results of evaluation indicate the following: (i) it is difficult to detect congestion promptly only by blood flow measurement; and (ii) it is effective to determination congestion by comprehensive evaluation of measurement results of both a blood flow and a color. Further, the above results of evaluation indicate that in the case of ischemia as with the case of congestion, color information is also important for detecting decrease of blood flow in the case of incomplete blocking of blood flow.

The above evaluation results show that in color measurement for detecting a blood flow disorder, use of a combination of a red color component and a green color component was very effective. In contrast, a blue color component was found to be less useful. Further, the above evaluation result indicated the necessity and usefulness of detection of a blood flow disorder by use of a combination of measurement of pulse waves or heartbeats and color measurement. Further, in regard to the color of a living tissue, the color of a living tissue changes depending on the postoperative course after transplantation, also when the state of a flap improves. Furthermore, the color of a living tissue changes both in a healthy portion and in a flap portion in response to environmental temperatures, meals, administration of drugs, etc. Therefore, it is very effective to simultaneously evaluate not only the color of a flap portion but also the color of a healthy portion adjacent to the flap portion so as to determine a blood flow disorder in the flap portion, on the basis of a color change in the flap portion relative to that in the healthy portion.

Further, the temperature of a living tissue as well as pulse waves or heartbeats and the color of the living tissue is an important indicator of a blood flow state. Since the temperature of a living tissue is largely affected by transfer of heat due to blood flow and supply of oxygen and nutrients via blood flow, the temperature of the living tissue is useful as blood flow information. Therefore, measuring the temperature of a living tissue and analyzing the temperature together with pulse waves or heartbeats or the color of the living tissue make it possible to analyze various aspects of a blood flow state and to remarkably improve precision and reliability of diagnosis. In a case where a plurality of pieces of blood flow information is measured as a two-dimensional distribution by providing temperature sensors such as thermistors arranged together with optical sensors in a sensor sheet, a two dimensional blood flow state can be grasped.

One or more embodiments of the present invention can highly reliably detect blood flow disorders such as congestion and ischemia in an invisible environment (e.g., an area under clothes and the inside of a body), being attached to a transplanted living tissue for a long time without putting a mechanical load on the transplanted living tissue having a non-flat three-dimensional curved surface.

REFERENCE SIGNS LIST 10 sensor sheet; 11 substrate; 12 optical sensor; 20 control device; 30 computer; 40, 50, and 60 optical sensor; 71 protective tape; 72 sensor sheet: and 100 blood flow disorder detection device

What is claimed is:

1. A blood flow disorder in a transplanted tissue detection device, comprising:
   a sensor sheet comprising a flexible substrate and a plurality of sensors provided on the flexible substrate; and
   an analyzer that is configured to analyze outputs of the plurality of sensors,
   wherein the sensor sheet is at least partially transparent and allows for observation of color of the transplanted tissue and a healthy tissue in a state in which the sensor sheet is configured to attach to the transplanted tissue and the healthy tissue,
   wherein the plurality of sensors are configured to measure different types of blood flow information of the transplanted tissue and the healthy tissue, the blood flow information being obtained by attaching the sensor sheet to at least a portion of the transplanted tissue and at least a portion of the healthy tissue, and
   wherein the blood flow information is selected from the group consisting of pulse waves, heartbeats, color of the transplanted tissue and the healthy tissue, temperature of the transplanted tissue and the healthy tissue, and combinations thereof, and
   wherein the analyzer is configured to detect blood flow disorder selected from the group consisting of congestion, ischemia, and combinations thereof in the transplanted tissue by analyzing the different types of blood flow information from the plurality of sensors.

2. The blood flow disorder detection device according to claim 1, wherein one of the plurality of sensors are configured to measure pulse waves or heartbeats as the blood flow information.

3. The blood flow disorder detection device according to claim 1, wherein one of the plurality of sensors are configured to measure color of the transplanted tissue and the healthy tissue as the blood flow information.

4. The blood flow disorder detection device according to claim 1, wherein one of the plurality of sensors are configured to measure temperature of the transplanted tissue and the healthy tissue as the blood flow information.

5. The blood flow disorder detection device according to claim 1, wherein the plurality of sensors comprise:
   a first sensor comprising a light-emitting element and a light-receiving element, wherein the first sensor is configured to measure pulse waves or heartbeats by detecting a color specifically absorbed by blood; and
   a second sensor comprising a light-emitting element and a light-receiving element, wherein the second sensor is configured to measure color of the living tissue by detecting at least two different colors.

6. The blood flow disorder detection device according to claim 5, wherein the first sensor is configured to use green light and the second sensor is configured to use red light and green light.

7. The blood flow disorder detection device according to claim 1,
   wherein the sensor sheet further comprises a transparent adhesive layer, and
   wherein the sensor sheet is a laminate comprising the transparent adhesive layer.

8. A blood flow disorder in a transplanted tissue detection device, comprising:
   a sensor sheet comprising a flexible substrate and a plurality of sensors provided on the flexible substrate; and an analyzer that is configured to analyze outputs of the plurality of sensors, wherein the sensor sheet is at least partially transparent and allows for observation of color of the transplanted tissue and a healthy tissue in a state in which the sensor sheet is configured to attach to the transplanted tissue and the healthy tissue, and wherein the sensors are optical sensors and shielded from light, and wherein a substrate surface on an opposite side of the flexible substrate surface where the sensors are provided is non-transparent and masked so as to be a color similar to skin to reduce contrast of color and/or luminance between the device and the skin, and wherein the plurality of sensors are configured to measure different types of blood flow information of the transplanted tissue and the healthy tissue, the blood flow information being obtained by attaching the sensor sheet to at least a portion of the transplanted tissue and at least a portion of the healthy tissue, and wherein the blood flow information is selected from the group consisting of pulse waves, heartbeats, color of the transplanted tissue and the healthy tissue, temperature of the transplanted tissue and the healthy tissue, and combinations thereof, and wherein the analyzer is configured to detect a blood flow disorder selected from the group consisting of congestion, ischemia, and combinations thereof in the transplanted tissue by analyzing the different types of blood flow information from the plurality of sensors.

* * * * *